US006800288B2

(12) United States Patent
Ferko et al.

(10) Patent No.: US 6,800,288 B2
(45) Date of Patent: Oct. 5, 2004

(54) RECOMBINANT INFLUENZA A VIRUSES

(75) Inventors: Boris Ferko, Wiener Neudorf (AT);
Andre Egorov, Vienna (AT); Regina Voglauer, Vienna (AT)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 0 days.

(21) Appl. No.: 10/204,664

(22) PCT Filed: Mar. 2, 2001

(86) PCT No.: PCT/EP01/02392

§ 371 (c)(1),
(2), (4) Date: Oct. 30, 2002

(87) PCT Pub. No.: WO01/64860

PCT Pub. Date: Sep. 7, 2001

(65) Prior Publication Data

US 2003/0147916 A1 Aug. 7, 2003

(30) Foreign Application Priority Data

Mar. 2, 2000 (EP) .......................................... 00104338

(51) Int. Cl.[7] .................... A61K 37/145; A61K 39/295; C12N 7/01; C12N 15/44; C12N 15/62; C12N 15/86
(52) U.S. Cl. ............................... 424/199.1; 424/209.1; 424/192.1; 424/188.1; 435/320.1; 435/235.1; 435/236; 435/471; 435/472; 536/23.72; 536/23.4
(58) Field of Search ........................... 424/199.1, 192.1, 424/209.1, 188.1; 435/320.1, 235.1, 236, 471, 472; 536/23.72, 23.4

(56) References Cited

U.S. PATENT DOCUMENTS 5,843,724 A * 12/1998 Krug et al. ................. 435/69.7
6,573,079 B1 * 6/2003 Palese et al. ............ 435/235.1
6,669,943 B1 * 12/2003 Palese et al. ............ 424/199.1

FOREIGN PATENT DOCUMENTS

WO    WO 99/64068 A1    12/1999
WO    WO 99/64571 A1    12/1999

OTHER PUBLICATIONS

Frischmeyer et al. Human Molecular Genetics 8(10): 1893–1900, 1999.*
Egorov et al (Journal of Virology 72:6437–6441, 1998).*

Ferko et al (Journal of Infectious Diseases 178(5): 1359–1368, 1998).*

Ferko et al (Journal of Human Virology 3(5): 253, Sep. 2000) (Abstract only).*

Egorov et al., VOPR Virusol vol. 39, No. 5, 201–5, 1994 (w/abstract).

Egorov et al., Transfectant Influenza A Viruses with Long Deletion in the NSI Protein Growth Efficiently in Vero Cells, Journal of Virology, vol. 72, No. 8, Aug. 1998, pp. 6437–6441.

Luytjes et al., "Amplification, Expression, and Packaging of a Foreign Gene by Influenza Virus", CELL, vol. 59, No. 6, Dec. 22, 1989, pp. 1107–1113.

Mattion et al., "Foot–and–Mouth Disease Virus 2A Protease Mediates Cleavage in Attenuated Sabin 3 Poliovirus Vectors Engineered for Delivery of Foreign Antigens", Journal of Virology, vol. 70, No. 11, Nov. 1996, pp. 8124–8127.

Percy et al., "Expression of a Foreign Protein by Influenza A Virus", Journal of Virology, vol. 68, No. 7, Jul. 1994, pp. 4486–4492.

Power et al., "A valid ELISPOT assay for enumeration of ex vivo, antigen–specific, IFN γ–producing T cells", Journal of Immunological Methods, vol. 227, 1999, pp. 99–107.

* cited by examiner

*Primary Examiner*—Mary E. Mosher
(74) *Attorney, Agent, or Firm*—Oliff & Berridge, PLC

(57) ABSTRACT

The invention relates to a recombinant NS gene of an influenza A virus comprising a functional RNA binding domain and a gene sequence modification after nucleotide position 400 of the NS1 gene segment, counted on the basis of influenza A/PR/8/34 Virus, wherein the modification bars transcription of the remaining portion of the NS1 gene segment. It further relates to embodiments, wherein the modification comprises deletions, insertions, or a shift of the open reading frame, and particularly to constructs comprising an insertion of an autocleavage site 2A, the nef gene from HIV-1 or the sequence encoding the ELDKWA-epitope of gp41 of HIV-1. The invention also relates to influenza virus transfectants that contain the modified NS gene and have an IFN inducing phenotype but which may or may not be sensitive towards IFN. The invention also relates to vaccines comprising such a chimeric virus.

27 Claims, 12 Drawing Sheets

US 6,800,288 B2

RECOMBINANT INFLUENZA A VIRUSES

TECHNICAL FIELD

The invention is in the fields of vaccine development and application and relates to attenuated live vaccine vectors, more specifically to such vectors based on or derived from genetically modified influenza A virus strains, and to the manufacture of recominant influenza viruses and vaccines.

BACKGROUND OF THE INVENTION

Influenza viruses are segmented negative-strand RNA viruses and belong to the Orthomyxoviridae family. Influenza A virus consists of 9 structural proteins and codes additionally for one nonstructural NS1 protein with regulatory functions. The non-structural NS1 protein is synthesized in large quantities during the reproduction cycle and is localized in the cytosol and nucleus of the infected cells. The segmented nature of the viral genome allows the mechanism of genetic reassortment (exchange of genome segments) to take place during mixed infection of a cell with different viral strains. Several features make influenza viruses attractive candidates for the development of effective live vaccine vectors against different diseases:

(i) influenza viruses induce strong cellular and humoral immune responses, at the systemic and the mucosal level against viral proteins following infection;

(ii) influenza virus as an RNA virus does not contain a DNA phase in its replication cycle. Therefore chromosomal integration of viral genes into the host can be excluded;

(iii) many different influenza virus subtypes are available. Since antibodies against these different subtypes show no or little crossreactivity, pre-existing immunity to the viral vector in the host, which is frequently a problem for other live vectors, can be circumvented. Also, effective booster immunizations with different subtype influenza viruses expressing the same antigens might be possible; and (iv) attenuated influenza viruses as live influenza vaccines, which were shown to be safe and immunogenic in humans, are available.

Until now the main problem of utilizing influenza virus as a vector concerns the size of the virus genome and its limited capacity to tolerate foreign sequences. Among ten influenza viral proteins, only the surface glycoproteins haemagglutinin (HA) and neuraminidase (NA) have been successfully engineered for stable expression of foreign epitopes. Since influenza virus tolerates an insertion of only approximately 10 amino acids into its HA molecule, there is only a limited possibility to influence the conformation properties of inserted epitopes which would probably be better presented if longer sequences would be introduced. Besides, surface influenza glycoproteins such as HA or NA cannot be considered as optimal targets for the presentation of foreign sequences because of their association with antigenic properties of the viruses. An HA live virus construct containing a desired foreign antigen is not applicable for boosting immunizations (e.g., by second and further administrations) because of the pre-existing immunity against the HA caused by the first immunization or by a natural virus infection. A booster immunization would be possible only upon introduction of the desired antigenic structure into another HA molecule belonging to a different influenza virus subtype. It is evident that such a process is difficult, laborious and extremely time consuming and therefore unlikely to be suitable for routine vaccine preparation Preceding investigations in connection with the present invention have indicated that the NS gene of influenza A virus may be a promising alternative to HA as a viral carrier for presenting a desired foreign antigen to the animal or human immune system. The recently established method of reverse genetics (Egorov et al., 1998, J Virol 72(8), 6437–41) allows to rescue influenza viruses containing long deletions or insertions of foreign sequences at the carboxyl side of the non-structural Protein 1 (NS1 protein). NS1 protein is abundant in influenza virus-infected cells and stimulates cytotoxic T-lymphocyte (CTL) responses as well as antibody responses during the natural course of influenza virus infection.

Further details about the influenza virus NS gene can be found in WO 99/64571. Additionally, WO 99/64571 discloses that attenuated influenza A virus transfectants containing knockout deletions of the entire NS1 gene were found to have a strong interferon (IFN) inducing phentopye. This was concluded from the finding that such transfectants were able to grow on IFN deficient Vero cells but were unable to grow on hen eggs or Madin-Darby Canine Kidney (MDCK) cells.

The influenza NS1 protein is an RNA-binding protein which has been implicated in a number of regulatory functions during influenza virus infection. It is synthesized in large amounts and found mainly in the nucleus early during infection and later in the viral cycle in the cytoplasm of the infected cells. Other than the influenza NS-1 protein, another regulatory viral protein, namely the Nef protein of HIV-1 which is a myristylated protein, is localized in the cytosol in association with the cell membrane.

An immune response directed against early expressed regulatory HIV-1 proteins could possibly allow the elimination of virus-infected host cells in the replication cycle before release of new infectious viral particles would even occur. As the Nef protein is among the first ones to be released and further is one of the major HIV proteins produced following infection, it could play a crucial role in developing an efficacious anti-AIDS vaccine.

The HIV-1 "negative factor" (Nef) is encoded by an open reading frame which is located at the 3' end of the virus, partially overlapping the U3 region of the 3' long terminal repeat. Up to 80% of the early, multiply spliced class of viral transcripts encode Nef. The Nef gene product is an $NH_2$-terminally myristylated protein of 27 to 30 kDa, which is predominantly localized in the cytoplasm and associated with the membrane and the cytoskeletal matrix. It is well conserved among the different human (HIV-1 and HIV-2) and Simian immunodeficiency viruses (SIV).

The close evolutionary relationship between these primate lentiviruses suggests that the Nef protein plays an important role in viral infection and pathogenesis, although the exact role in the virus life cycle and its functions at the cellular level are still the subject of current research.

Various details about the Nef protein and its effects are already known, however. For instance, it is reported that some humans infected with Nef-deleted, HIV remained disease-free, with normal CD4 counts 10 to 14 years after infection, although deletion of Nef is not a universal finding in long-term nonprogressors. In addition, Nef-deficient SIV fails to produce AIDS in infected adult macaques. SIV mutants deleted for the Nef gene even induce protection against a virulent challenge. Nef was shown to stimulate HIV-1 proviral DNA synthesis and its expression has also been found to induce the efficient internalization and degradation of the cell surface CD4 receptor for HIV-1. This Nef-induced CD4 down-regulation, which renders cells resistant to viral superinfection, has the potential to increase virus replication by facilitating release of progeny virions. It was further demonstrated that extracellular Nef protein could activate HIV-1 from latent to productive infection both in infected T-cell lines and in PBMC from asymptomatic carriers. Further, it was shown that CTLs inefficiently lysed primary cells infected with HIV-1, if the viral Nef gene product was expressed.

Protection of HIV-infected cells from efficient recognition and killing by CTLs correlates with the Nef-mediated down-regulation of MHC class I molecules. Nef also interferes with the induction of IL-2 mRNA in T-cell lines. Furthermore, there are a large number of cellular partners that have been found to be associated with Nef expression including Src family kinases, β-COP, a serine-threonine kinase, thioesterase and p53.

It is also reported that the majority (about ⅔) of HIV-1 seropositive patients generated Nef-specific CTLs.

Two central multirestricted immunodominant regions (amino acids 66 to 100 and 115 to 146) and a carboxyl-terminal region (amino acids 182 to 206) were identified within the Nef protein. These three multirestricted immunodominant regions (amino acid sequences containing more than one T-cell epitope) are being recognized by human CD8+CTLs in association with at least 14 different MHC class I molecules including the important MHC haplotypes HLA-A1, -A3, -A11, -B8, -B17, -B18 and -B37.

The two central multirestricted domains of the Nef protein are the most highly conserved regions among different HIV-1 isolates and were imrnunodominant for most of the asymptomatic HIV-1 seropositive donors tested. In addition to the high immunogenicity of the HIV-1 Nef protein, which has been demonstrated by its capacity to induce strong T-cell immune responses, also Nef-specific B-cell immune responses are reported in the literature.

SUMMARY OF THE INVENTION

The present invention relates to the development of attenuated live vaccine vectors, more specifically to such vectors based on or derived from genetically modified influenza A virus strains. It further relates to the construction and modification of genetically engineered non-structural genes of influenza A viruses, particularly of the NS1 gene segment, wherein the modifications include deletions of selected parts of the NS1 gene segment and/or insertions of heterologous, preferably antigenic, sequences into selected sites of the NS1 gene. It is another objective of the invention to provide chimeric influenza viruses containing such modified NS1 gene segments but which do not suffer from the drawback of being IFN sensitive, in contrast to the transfectants disclosed in WO 99/64571. The invention further relates to recombinant proteins obtained from the NS1-modified viruses by expression in a suitable host system and further to a vaccine comprising the NS1-modifed viruses of the present invention.

It is yet another objective of the invention to provide a method for obtaining recombinant influenza viruses as well as attenuated influenza vaccines, based on the generation of continues cell lines (e.g. Vero, MDCK etc.) expressing synthetic influenza genes (minus sense RNA) comprising natural or engineered influenza sequences (deletions or insertions). These cell lines producing high quantities of such genes can be used for infection with influenza virus followed by selection procedures in order to get a gene of interest incorporated into the viral progeny.

The present inventors have established a reverse genetics system on Vero cells allowing them to manipulate the virulence of the PR8 influenza A virus strain by changing the length of the translated NS1 protein. In the course of the research leading to the present invention the capacity of influenza A virus to tolerate and present long insertions in the NS gene have been investigated. A collection of several chimeric NS1 gene constructs using heterologous sequences including the HIV-1 derived sequences encoding ELDKWA (SEQ ID NO: 1) of gp41 or Nef, has been established by insertion of one or more of the heterologous sequences or, optionally, several repeats of any such sequence, in frame into the NS1 protein.

The aforementioned heterologous sequences were inserted downstream nt position 400 (corresponding to aa position 124) and optionally preceded by the 2A autocleavage site sequence and/or by a leader sequence derived from the influenza HA molecule. Other constructs additionally comprised an anchor sequence derived from the influenza HA molecule as an insertion right after the desired antigenic sequence(s), thus forming the end of the entire heterologous insertion. In each case the insertions were followed by a stop codon to prevent transcription and translation of the remaining portion of the NS1 gene segment (including the effector domain), while maintaining the cleavage site for the NS splicing (necessary for transcription and translation of the NS2=NEP gene segment) fully functional.

Rescued viruses caused expression and accumulation of the foreign antigens in the cytosol and/or on the surface of the infected cells. The inventors also successfully rescued transfectant viruses harbouring a multirestricted immunodominant region rich in T-cell epitopes of HIV-1 Nef protein (136 amino acids).

All transfectants displayed normal growth characteristics in Vero cells, embryonated chicken eggs and MDCK cells, but were attenuated in mice. Chimeric influenza NS1-Nef viruses did not replicate in respiratory tracts of infected mice, but were able to induce a strong Nef-specific CTL response following a single intranasal immunization. In addition, a Nef-specific antibody response was detected following three immunizations. Transfer of the recombinant NS-nef gene by genetic reassortment from the viral PR8 (influenza A/PR/8/34; Egorov et al., 1994, Vopr. Virusol. 39:201–205) vector to other influenza strains resulted in the same level of attenuation and immunogenicity. This finding permitted the present inventors to perform effective boosting immunizations using several attenuated vectors of different antigenic subtypes.

Thus, the inventors were able to demonstrate that the approach to create a set of influenza chimeric strains belonging to different influenza subtypes while bearing the identical recombinant chimeric NS1 gene, gives the opportunity to create several strains for boosting immunizations. They have further proven that once a new chimeric NS1 gene construct is rescued it can be routinely transferred to another influenza strain by genetic reassortment.

DETAILED DESCRIPTION OF THE INVENTION

Figure 1:
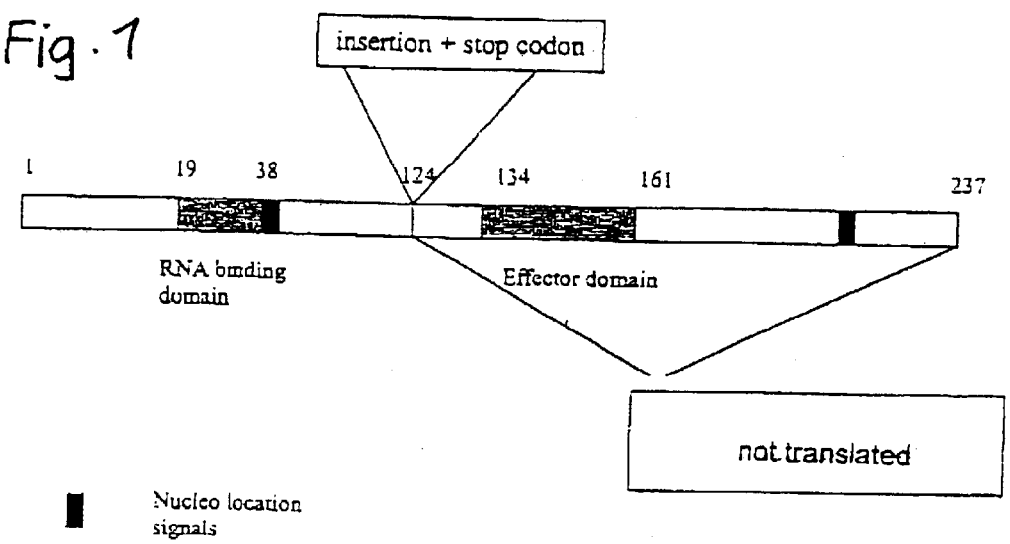
FIG. 1 shows a functional map of the engineered NS1 protein of PR8.

In one embodiment, the invention relates to genetically engineered NS gene constructs of an influenza A virus comprising sequence modifications, i.e. deletions or insertions, between nucleotide (nt) positions 400 and 525 of the NS1 gene segment (numbering is based on the NS gene of influenza A/PR/8/34 virus). Unexpectedly, it turned out that maintaining functionality of the NS1 gene segment up to nt position 400 (corresponding to aa position 124 of the NS1 protein) while concomitantly deleting the remaining portion or at least a major part thereof or inserting a foreign nt sequence into the region after nt position 400 or shifting the reading frame to cause wrong transscription and translation of the remaining NS1 portion resulted in the rescue of NS gene constructs that rendered their viral vectors IFN inducing but not IFN sensitive.

This surprising finding was confirmed by experiments wherein the chimeric influenza viruses engineered according to the present invention not only induced a strong IFN response in MDCK cells and hen eggs but were also able to grow on these host substrates at an efficiency comparable to the wildtype PR8 virus. In contrast, chimeric influenza viruses containing deletions of the first third of the NS1 gene or deletions of the entire NS1 gene displayed an IFN inducing as well as an IFN sensitive phenotype. They were unable to grow on hen eggs or MDCK cells and therefore could only be cultivated on IFN deficient cell lines such as Vero cells. Chimeric influenza viruses of the latter type have been disclosed in WO 99/64571. It is assumed that the viruses of the present invention, which are not as strongly attenuated as the viruses of WO 99/64571, are more immunogenic and therefore better suitable for the manufacture of highly effective live vaccines against various kinds of viral infections.

In another embodiment of the invention the genetically engineered NS gene is used as a genomic fragment of influenza A virus in a method wherein it is transferred to any desired influenza A virus strains or live influenza vaccines by means of genetic reassortment. In this context, it is preferred that the genetically engineered NS gene is established as a cDNA clone that can be transferred to any influenza A virus strain or live influenza vaccine as a genomic fragment by means of reverse genetics methods. For example, another vector such as Aichi/NS-Nef belonging to the H3N2 subtype, but containing the same recombinant NS-gene, can be obtained in this manner. In contrast to strategies generating recombinant influenza viruses expressing foreign antigens in the context of HA or NA molecules, this approach enables a fast generation of a set of non-crossreactive vectors for optimal boosting immunizations.

In a preferred embodiment of the invention the genetically engineered NS gene is designed for the expression of viral antigens, particularly for expression of the HIV-1 sequences of Nef or ELDKWA (SEQ ID NO: 1) of gp-41.

In another embodiment of the invention the genetically engineered NS gene is rescued as a genomic fragment of influenza virus expression of which contributes as or elicits a factor of protein kinase p-68 (PKR) over-expression and activation in infected cells.

In another embodiment of the invention the chimeric NS gene is part of an attenuated (cold adapted) live influenza vaccine vector wherein the genetically engineered NS gene is the main factor or an additional factor of attenuation. It is particularly useful for the manufacture of safe and highly effective, influenza virus-based vaccines including but not restricted to anti-HIV-1 vaccines, wherein the transfected chimeric NS gene construct comprises gene sequences of nef, 2A, and/or gp-41 or other viral antigens, for the induction of strong antibody and/or B- and T-cell immune responses.

The vaccine comprising an attenuated (cold adapted) live influenza virus vector can be prepared in a suitable pharmaceutical formulation and may be used for prophylactic immunizations as well as for therapeutic vaccination, including induction of IFN release in combination with a stimulation of B- and T-cell response. In such formulations influenza vectors might be used in combination with any other vector expressing analogous antigens to ensure a maximum booster effect. Thus, generating of attenuated influenza NS vectors offers the possibility to obtain novel recombinant vaccines with nearly optimal balance of safety and immunogenicity directed against a broad range of pathogens.

In a particular embodiment of the invention the genetically engineered NS gene of an influenza A virus comprises a heterologous nucleotide insertion derived from the HIV-1 nef gene (nucleotides 210–618 of the nef gene of the HIV-1 clone NL4-3) plus an insertion of the autocleavage sequence 2A (54 nucleotides) N-terminally to the HIV-1 derived insertion at the position 400 of the NS protein. Elimination of the first 68 amino acids of the Nef protein was done to exclude domains comprising the myristoylation site and other domains associated with pathogenic properties of the multifunctional HIV-1 Nef protein.

In further experiments the inventors found that influenza PR8/Nef virus and influenza Aichi/Nef virus resulted in a high titer of antibodies against the viral vector and a less but still significant titer against the nef gene. The PR8/Nef virus is a PR8-124 virus with truncated NS1 containing a 2A autocleavage sequence after aa position 124 of the NS1 protein which additionally comprises a nef sequence (aa 70-206 of HIV-1 Nef protein) following the autocleavage site. The Aichi virus is reassorted in that except for the NS gene all genes including the genes encoding the envelope proteins HA and NA originate from H3N2 Aichi wild type virus, while the recombinant NS gene originates from the PR8/Nef virus. It was also observed that the PR8/Nef and Aichi/Nef viruses caused strong T-cell responses against the nef gene as well as the viral vector. This experiment proved that it is possible to transfer the chimeric NS gene into another influenza virus strain to elicit essentially the same immune response. This finding is important as it allows to provide for possibilities to boost immunizations and to design seasonal influenza vaccines with varying immunogenic subtypes but constant chimeric NS1 gene-based activity.

In another embodiment the invention provides for a method for generating recombinant influenza viruses by constructing a vector comprising a modified NS gene wherein the NS1 gene sequence is partially or entirely deleted or truncated, mixing said vector with lipids to allow self-assembling of lipid-DNA complexes and transfecting the lipid-DNA complexes into a desired continuous cell line, for example a Vero or MDCK cell line, and selecting clones that stably integrate and replicate the modified NS gene, which then are infected with any desired influenza strain, and particularly, with an epidemic wild-type influenza strain, to produce attenuated viral progeny containing said modified NS gene. In this method, the modified NS gene may further comprise insertions of heterologous gene sequences coding, for instance, for other viral antigens or pathogens e.g. such as the ones disclosed herein.

It is another object of the present invention to provide a method for rapid vaccine manufacture comprising the steps of transforming a continuous cell line to produce a desired synthetic viral gene, particularly a modified NS gene of influenza A virus wherein the NS1 gene is partially or entirely deleted or truncated, infecting the transformed cell line with a desired virus, particularly, with an epidemic wild-type influenza strain, to produce attenuated viral progeny containing said modified NS gene, selecting attenuated recombinant viruses and multiplying such viruses under conditions suitable for efficient virus replication, preferably using interferon-deficient substrates, and combining harvested virus material with a pharmaceutically acceptable carrier resulting in an anti-viral vaccine. In this method, the modified NS gene may further comprise insertions of heterologous gene sequences coding, for instance, for other viral antigens or pathogens e.g. such as the ones disclosed herein.

Further embodiments are defined in the dependent claims. In order that the invention described herein may be more fully understood, the following examples are set forth. The examples are for illustrative purposes only and are not to be construed as limiting this invention in any respect.

EXAMPLE 1

Preparation of Recombinant Negative Strand Influenza A Viruses ("Reverse Genetics Method")

Figure 2:
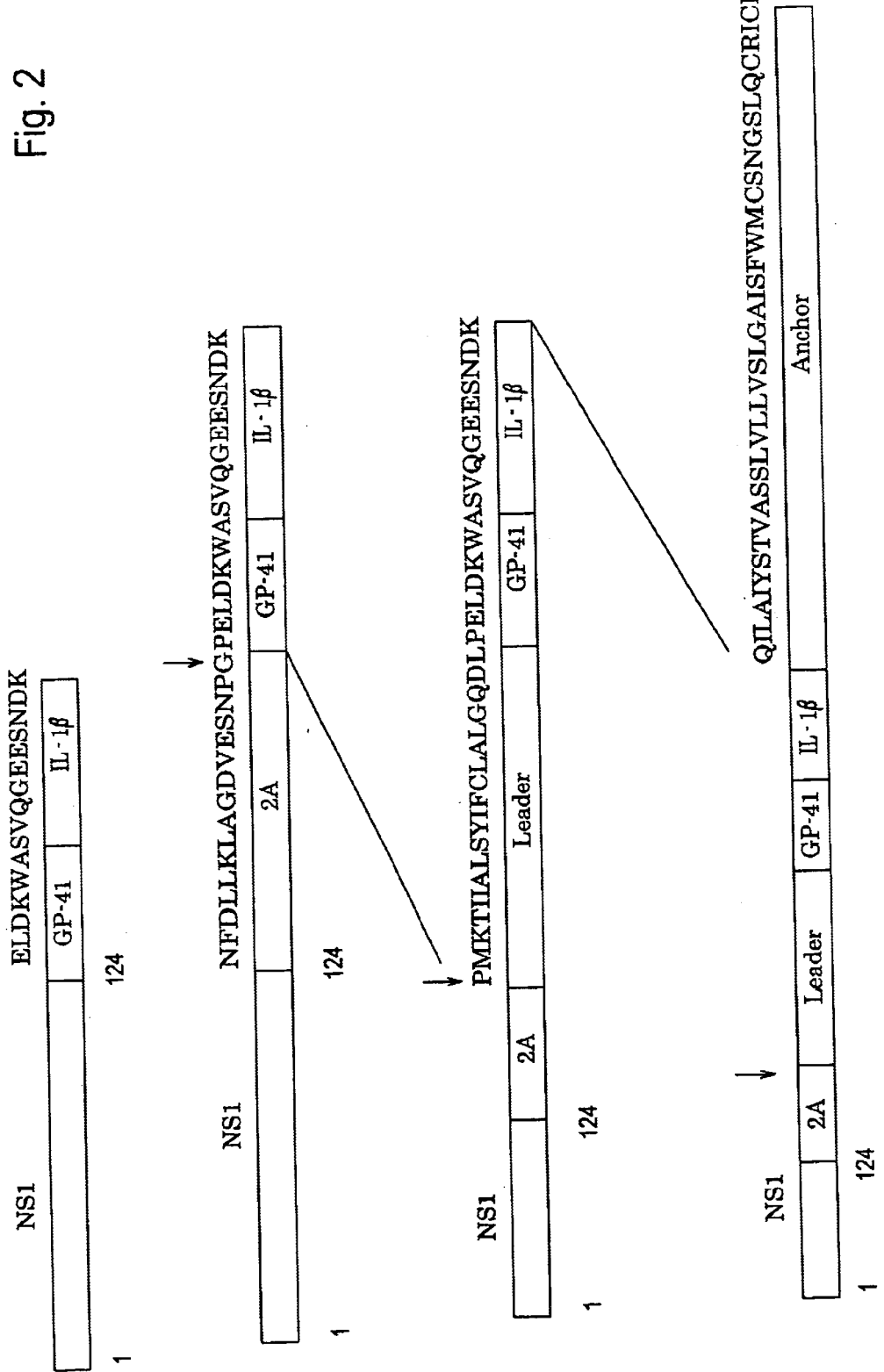
FIG. 2 shows the structure of recombinant NS1 proteins of the rescued influenza transfectant viruses expressing gp-41 and IL-1β peptides and depicts SEQ ID NOS: 7–10.

The plasmid clones containing the nef sequence have been prepared on the basis of the existing plasmid clone of influenza NS gene pUC19/NSPR (Egorov et al., 1998, J Virol 72/8, 6437–41). The nef sequence was inserted into the NS1 protein ORF, downstream of an additional sequence: a protease recognition sequence P2A (NFDLLKLAGDVESNPG/P) (SEQ ID NO: 2) derived from foot and mouth disease virus that is posttranslationally cleaved by an ubiquitous cellular protease (Mattion et al., 1996, J Ivrol 70(11), 8124–7; Percy et al., 1994, J Virol 68(7), 4486–92), so that the gp-41 molecule should be cleaved from the NS1 polypeptide and transported to the cell surface. The plasmid clone was used for synthesis of chimeric RNA to be transfected into Vero cells in order to rescue the recombinant influenza viruses. In the functional map of the engineered NS1 protein of the present invention (FIG. 1) it is indicated that the insertions are introduced after aa position 124 and followed by a stop codon which has in effect that the remaining adjacent portion of the NS1 gene segment (including the effector domain) rests untranslated. From FIG. 2 it can be understood how the desired antigenic or otherwise heterologous sequences (e.g. gp-41 and IL-1β sequences) may be arranged to yield immunogenic constructs that after transfection into a suitable viral vector, preferably a cold adapted influenza virus, could form the basis of an effective vaccine against various infectious diseases.

Figure 3:
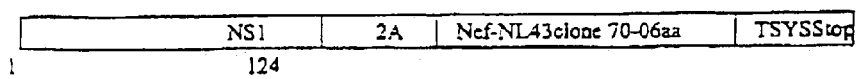
FIG. 3 shows the structure of recombinant NS1 protein of the rescued influenza transfectant PR82Anef (PR8/Nef) expressing aa70-206 of the Nef protein of HIV-1 NL4-3.

Analogously, FIG. 3 shows the arrangement of insertion of aa70–206 of the Nef protein HIV-1 NL4-3 into the NS1 protein of the rescued influenza transfectant PR82Anef (PR8/Nef).

In general, the experiments showed a tendency wherein the length of the heterologous insert or inserts was directly proportional to the degree of attenuation of the resulting virus strain. Additionally, the immunogenic potential of the expression products of larger inserts usually exceeded the one of smaller inserts. Therefore, it is preferred according to the present invention to make inserts encoding at least about 80 amino acids.

To create the chimeric Aichi/NS-Nef virus the RNA representing the recombinant NS segment of the PR8/NS-Nef virus was introduced into the genome of influenza A/Aichi/1/68 (H3N2) virus by a standard genetic reassortment performed on Vero cells utilizing rabbit polyclonal anti PR8 virus hyperimmune serum for selection. Genotyping of reassortants was performed by RT-PCR amplification and comparative restriction analysis of cDNA copies derived from each genome segment.

EXAMPLE 2

Transfection of Recombinant Viruses in Vero Cells

Synthetic negative sense RNA have been derived from plasmid clones by T3 transcription in the presence of purified viral RNP. Vero cells were previously infected with the helper influenza virus reassortant strain 25A-1 (H1N1, (Egorov et al., 1994, Vopr Virusol 39(5), 201–5) and then transfected with RNA complexes by DEAE-dextran transfection (Egorov et al., 1998, J Virol 72(8), 6437–41; Luytjes et al., 1989, Cell 59(6), 1107–13). Rescued transfectant viruses have been plaqued, purified on Vero cells 3 times, amplified on Vero cells and checked for biological properties.

Figure 10A:
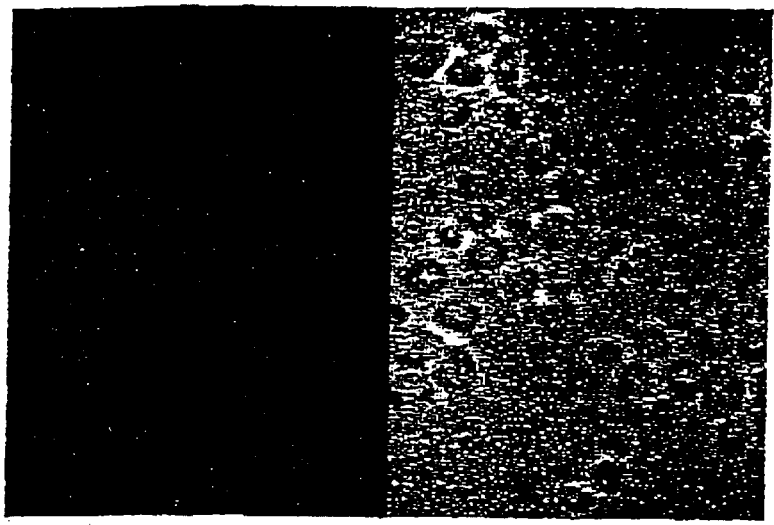
FIGS. 10a–10c show immunofluorescence of Vero cells infected previously with recombinant PR8/Nef virus (10a, 10b) and the wild type influenza PR8 virus (10c).
Figure 10B:
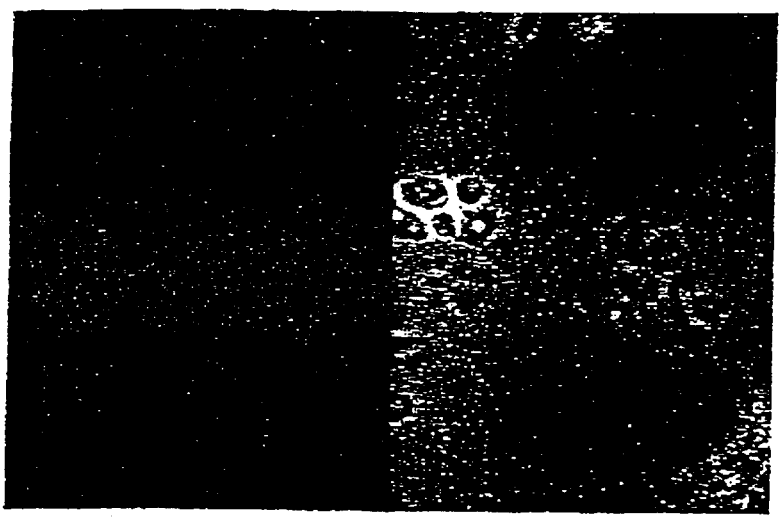
Figure 10C:
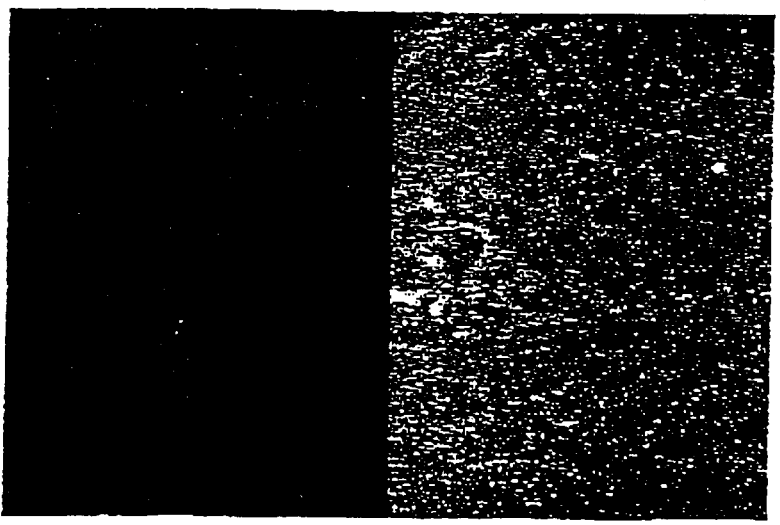

FIGS. 10a–c show immunofluorescence of Vero cells infected previously with recombinant PR8/Nef virus (MOI 0,01 in 10a and 0,1 in 10b) and the wild type influenza PR8 virus (10c). 24 hrs following infection cells were trypsinized and fixed on cover slides with 100% acetone. After several wash steps in PBS the slides were incubated for 40 min at 37° C. with a 1:50 dilution of anti Nef (aa179–195 epitope) mouse monoclonal antibody, then washed twice in PBS and incubated with 1:100 dilution of goat anti mouse IgG FITC conjugated antibody.

EXAMPLE 3

Immunization of BALB/c Mice

Figure 5:
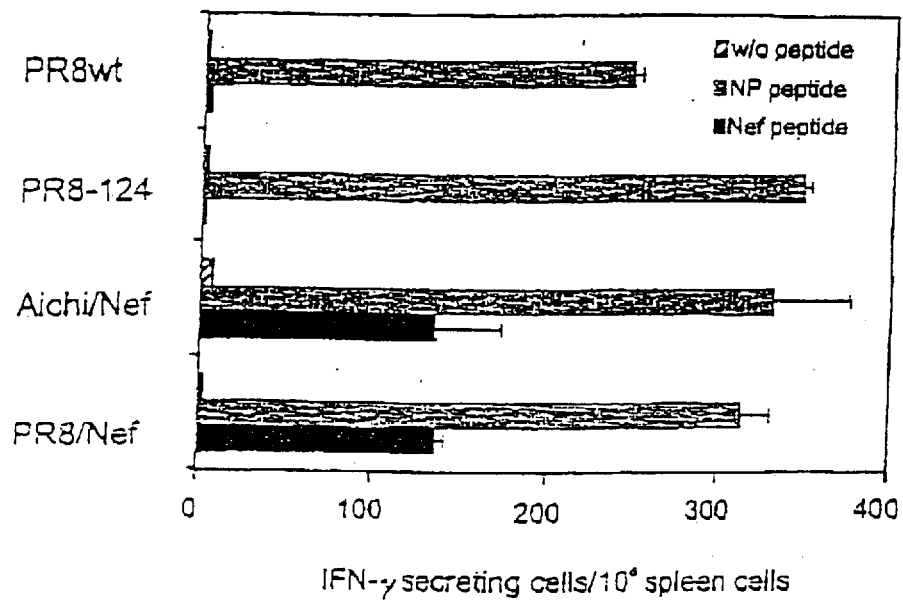
FIG. 5 shows the number of IFN-gamma secreting cells from immunized mice per $10^6$ spleen cells detected after immune spleen cells were incubated in the presence of Nef peptide, NP peptide or without peptide as an indicator for T-cell responses.

Groups of three BALB/c mice each were immunized with 2–5×10$^5$ PFU/mouse of influenza viruses PR8/Nef, Aichi/Nef; PR8-124 and with 4×10$^4$ PFU/mouse of the PR8 wt as indicated in FIG. 5. Spleen cells from immunized mice were obtained 9 days later and used as effector cells in the ELISPOT assay. FIG. 5 shows the number of IFN-gamma secreting cells per 10$^6$ spleen cells detected after immune spleen cells were incubated in the presence of the EWRFD-SRLAFHHVAREL peptide (Nef peptide)(SEQ ID NO: 3), TYQRTRALVRTMGD peptide (NP peptide) (SEQ ID NO: 4) or without peptide (w/o peptide). Results are expressed as average +/−SEM of duplicate cultures.

Figure 6:
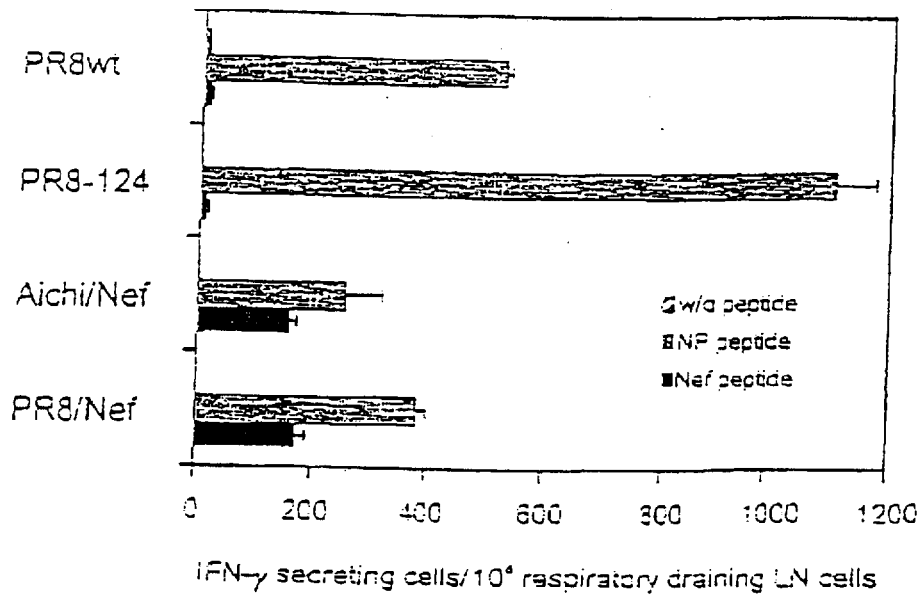
FIG. 6 shows the number of IFN-gamma secreting cells from the lymph nodes draining the respiratory tracts from immunized mice per $10^6$ spleen cells detected after immune spleen cells were incubated in the presence of Nef peptide, NP peptide or without peptide as an indicator for T-cell responses.

Groups of three BALB/c mice were immunized with 2–5×10$^5$ PFU/mouse of influenza virus PR8/Nef, Aichi/Nef; PR8-124 and 2×10$^4$ PFU/mouse of the PR8 wt as indicated in FIG. 6. Simple cell suspensions from the lymph nodes draining the respiratory tracts from immunized mice were obtained 9 days later and used as effector cells in the ELISPOT assay (Power et al, J Immunol Methods 227:99–107): Briefly, threefold serial dilutions of cell populations derived from murine spleens, draining lymph nodes and the urogenital tracts were transferred to wells coated with anti IFN-γ mAb (R4-6A2; BD PharMingen). Cells were incubated for 22 hours at 37° C. and 5% CO$_2$ in DMEM medium containing 10% FCS, IL-2 (30 U/ml), penicillin, streptomycin and 50 μM 2-ME in the presence of synthetic peptides. A biotinylated anti IFN-γ mAb (XMG1.2; BD PharMingen) was utilized as a conjugate antibody, then plates were incubated with streptavidin peroxidase (0.25 U/ml; Boehringer Mannheim Biochemica). Spots representing IFN-γ secreting CD8$^+$ cells were developed utilizing the substrate 3-amino-9-ethylcarbazole (Sigma) containing hydrogen peroxide in 0.1 M sodium acetate, pH 5.0. The spots were counted with the help of a dissecting microscope and results were expressed as the mean number of IFN-γ secreting cells±SEM of triplicate cultures. Cells incubated in the absence of synthetic peptides developed <10 spots/10$^6$ cells. Since depletion of CD8$^+$ cells resulted usually in >92% reduction of spot formation, cell separation was omitted in most assays. FIG. 6 shows the number of IFN-gamma secreting cells per 10$^6$ spleen cells detected after immune spleen cells were incubated in the presence of the EWRFDSRLAFHHVAREL peptide (Nef peptide)(SEQ ID NO: 3) TYQRTRALVRTMGD peptide (NP peptide) (SEQ ID NO: 4) or without peptide (w/o peptide).

Figure 4:
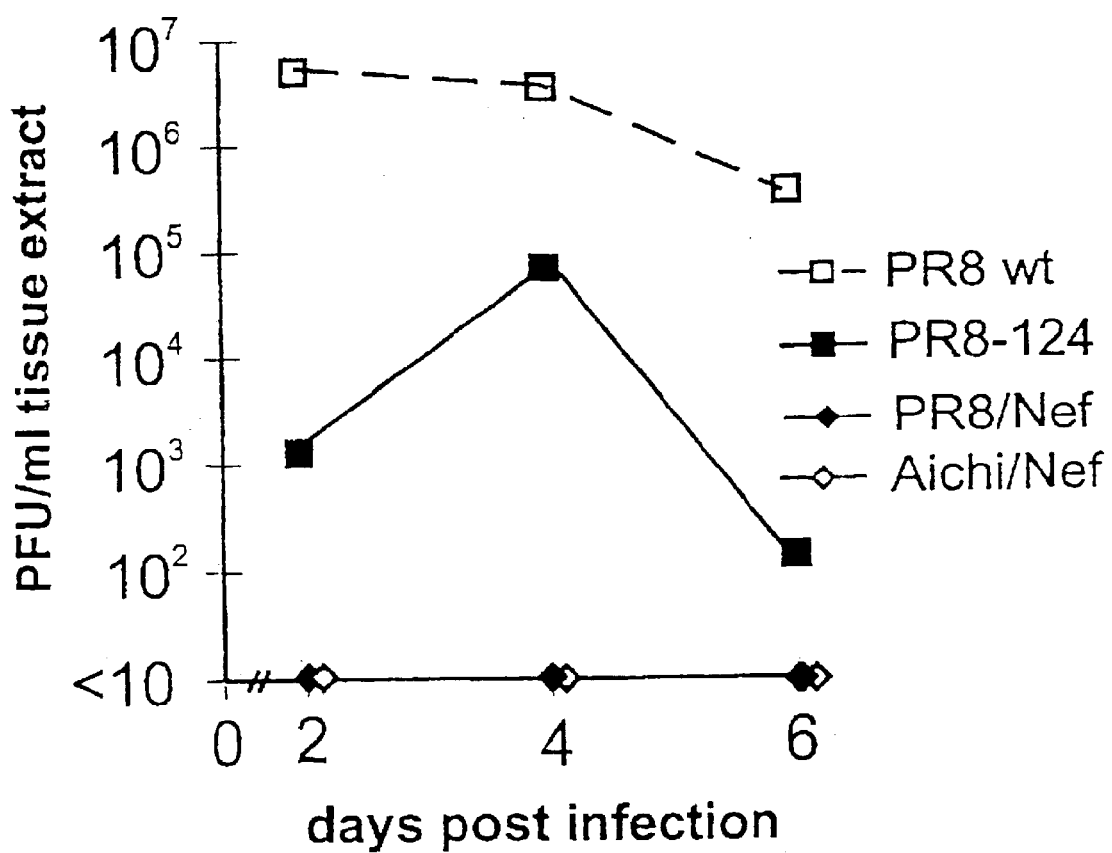
FIG. 4 shows the replication of chimeric influenza/Nef viruses in mouse lower respiratory tracts.
Figure 7:
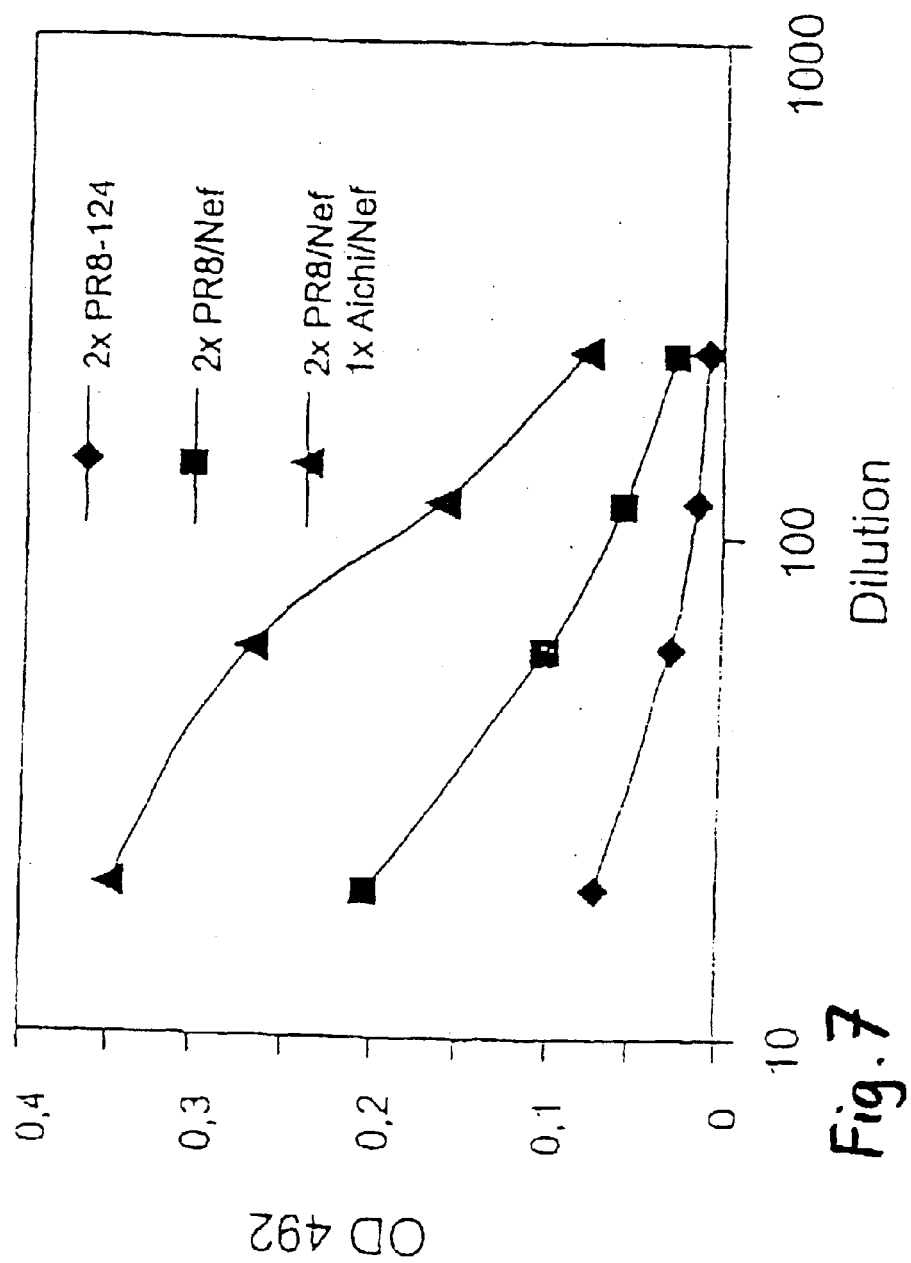
FIG. 7 shows Nef-specific serum IgG immune responses following $2^{nd}$ and $3^{rd}$ Immunizations of mice immunized with recombinant influenza/Nef viruses.

From FIG. 4, which shows the replication of the chimeric influenza/Nef viruses in mouse lower respiratory tracts, it can be understood that the PR8/Nef and Aichi/Nef viruses did not replicate in that tissue, hence were strongly attenuated, while at the same they were highly immunogenic to the mice causing strong T-cell and B-cell immune responses (as shown in FIGS. 5, 6 and 7). To characterize the insert (Nef peptide)-specific and vector (NP-peptide)-specific CD8$^+$ T cell response female BALB/c mice were immunized once or twice i.n. without narcosis with 10$^6$ PFU per animal of the PR8/NS-Nef, Aichi/NS-Nef; PR8/NS-124 or PR8 w.t. virus.

Figure 11:
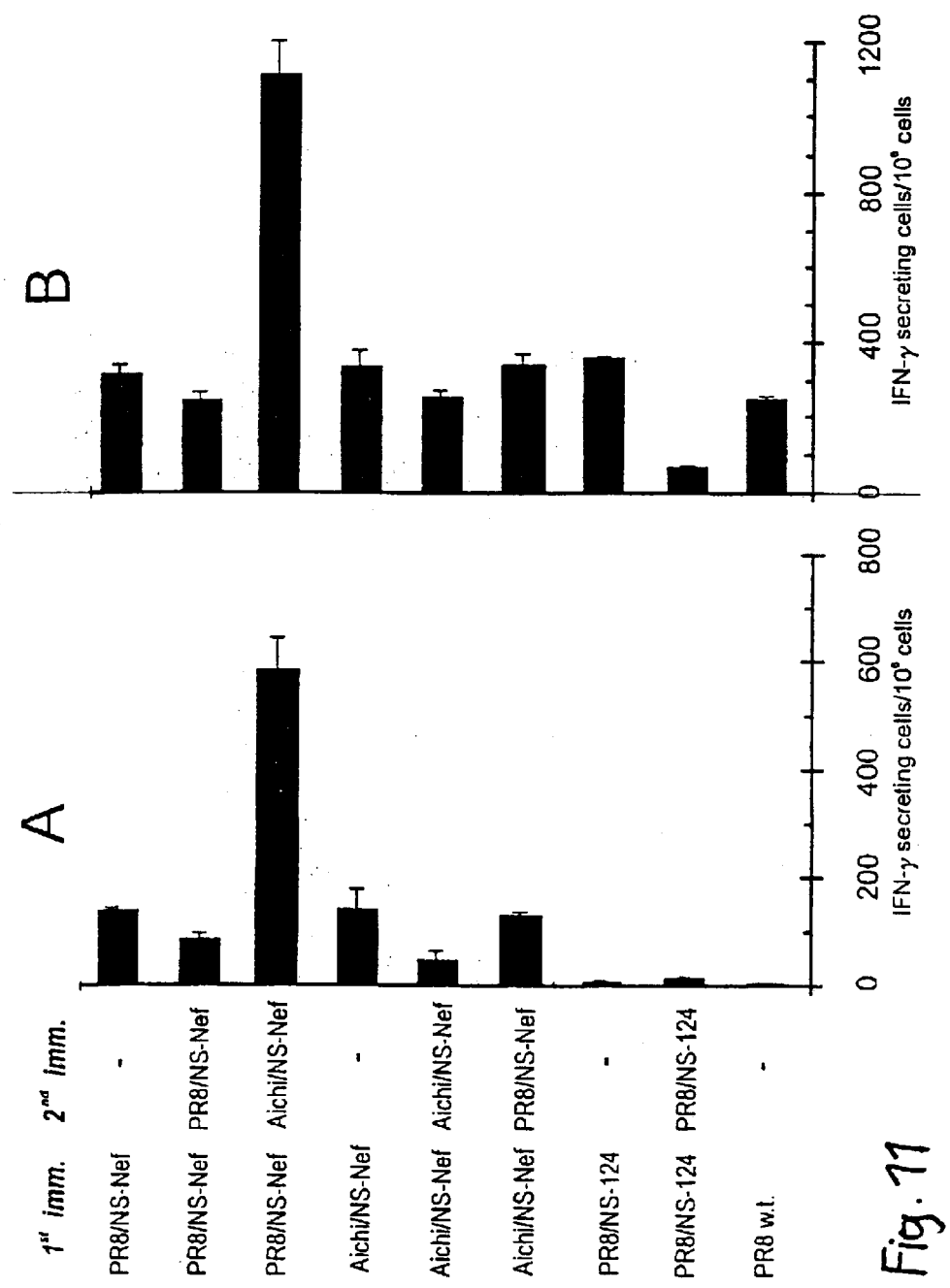
FIG. 11 shows Nef peptide-specific and NP peptide-specific immune responses as a quantification of IFN-γ secreting cells in murine spleen cells.

Three BALB/c mice per group were immunized once or twice i.n. in the absence of anesthesia with 10$^6$ PFU/mouse of influenza PR8/NS-Nef, Aichi/NS-Nef, PR8/NS-124 or PR8 w.t. as indicated in FIG. 11. The booster immunization was performed 21 days after priming. The single cell suspensions obtained 10 days after immunization from spleens of mice were assessed for Nef peptide-specific (A) or NP peptide-specific (B) IFN-γ secreting CD8$^+$ T cells in an ELISPOT assay. FIG. 11 shows the mean numbers of antigen-specific IFN-γ secreting cells±SEM of triplicate cultures.

Figure 12:
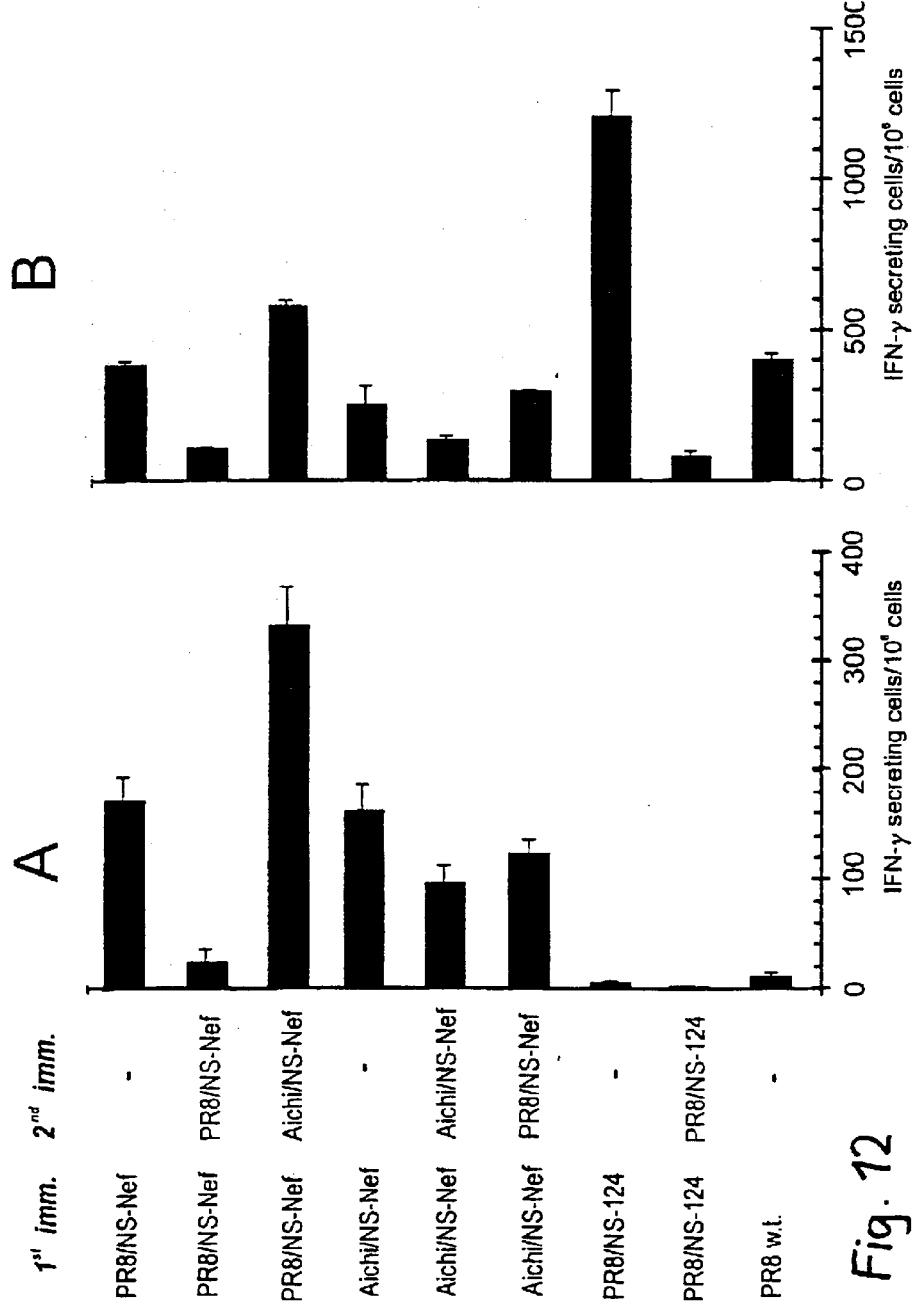
FIG. 12 shows Nef peptide-specific and NP peptide-specific immune responses as a quantification of IFN-γ secreting cells in lymph nodes draining the respiratory tracts of immunized mice.

Lymph nodes draining the respiratory tracts (mediastinal and retrobronchial lymph nodes) were collected 10 days after immunization from immunized BALB/c mice as described in the FIG. 11. Single cell suspensions were assessed for Nef peptide-specific (A) or NP peptide-specific (B) IFN-γ secreting CD8$^+$ T cells in an ELISPOT assay. FIG. 12 shows the mean numbers of antigen-specific IFN-γ-secreting cells±SEM of triplicate cultures.

Figure 13:
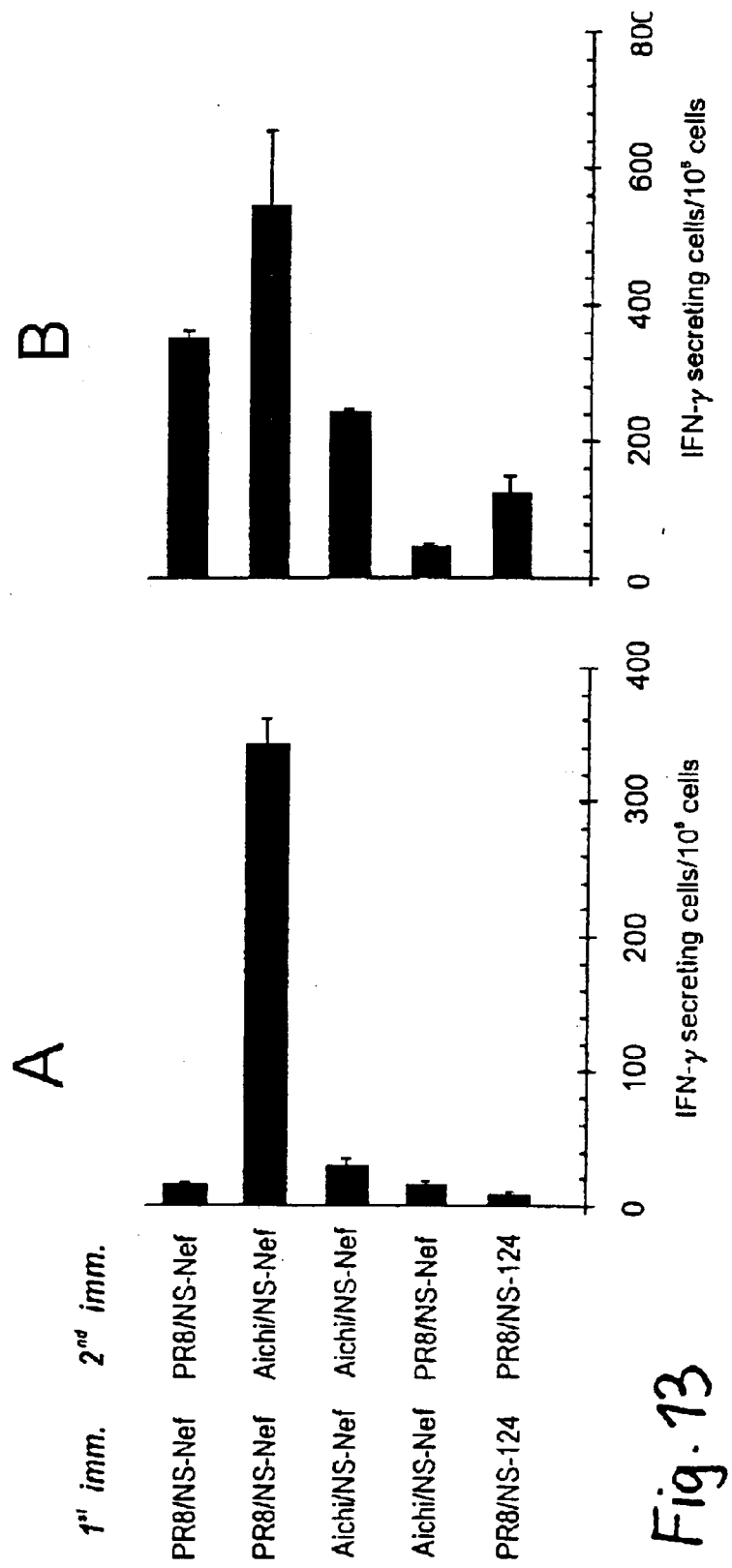
FIG. 13 shows Nef peptide-specific and NP peptide-specific immune responses as a quantification of IFN-γ secreting cells in urogenital single cell populations of immunized mice.

Three BALB/c mice per group were immunized twice i.n. in the absence of anesthesia with 10$^6$ PFU/mouse of influenza PR8/NS-Nef, Aichi/NS-Nef or PR8/NS-124 virus as indicated in FIG. 13. The booster immunization was performed 21 days after priming. The single cell suspensions derived 10 days after the second immunization from digested urogenital tracts (vagina, cervix, uterine horns and urethras) of immunized mice were assessed for Nef peptide-specific (A) or NP peptide-specific (B) IFN-γ secreting CD8$^+$ T cells in an ELISPOT assay. FIG. 13 shows the mean numbers of antigen-specific IFN-γ secreting cells±SEM of triplicate cultures.

Mice immunized once with either the PR8/NS-Nef or Aichi/NS-Nef virus induced significant numbers of Nef peptide-specific CD8$^+$ T cells in single cell suspensions derived from spleens (139±4 spots in PR8/NS-Nef immunized mice; 137±39 spots in Aichi/NS-Nef immunized mice; FIG. 11B) and lymph nodes (173±23 spots in PR8/NS-Nef immunized mice; 160±25 spots in Aichi/NS-Nef immunized mice; FIG. 12B). No relevant Nef peptide-specific CD8$^+$ T cell response was determined in both compartments of mice immunized with the PR8/NS-124 and PR8 w.t. viruses (the number of spots were always lower than 13; FIGS. 11B and 12B).

When vector (NP peptide)-specific CD8$^+$ T cell responses were compared, similar numbers of specific CD8$^+$ spleen cells were found in all groups of mice tested (FIG. 11A). In contrast to the systemic compartment (spleens), significant differences were obtained in the mucosa-associated respiratory lymph nodes. The replication competent PR8/NS-124 virus induced a markedly higher frequency of NP-peptide specific CD8$^+$ T cells whereas recombinant influenza/NS-Nef viruses and the pathogenic PR8 w.t. virus induced lower magnitudes of NP peptide-specific CD8$^+$ T cells (FIG. 12A).

In FIG. 7, which displays Nef-specific serum IgG immune responses of mice immunized with recombinant influenza/Nef viruses, the B-cell immune responses following 2nd and 3rd immunizations have been demonstrated to be strongest in the case where the mice have been immunized twice by PR8/Nef followed by a third immunization with Aichi/Nef, while the response was less prominent with twice immuniziations using the PR8-124 virus.

Further, a group of mice was primed i.n. with the PR8/NS-Nef virus and boosted 21 days later with the Aichi/NS-Nef virus. Another group of mice was immunized with the same viruses but in the reverse order. Data shown in FIGS. 11 and 12 indicate that the sequence in which the respective recombinant vectors were used for priming and boosting appeared to be crucial, since it was consistently observed that priming with the Aichi/NS-Nef (H3N2) followed by boosting with the PR8/NS-Nef (H1N1) induced a significantly lower number (approximately the range of the primary CD8+ T cell response) of the Nef peptide-specific and NP peptide-specific CD8+ T cells in spleens and draining lymph nodes when compared with the reverse order of immunization. A strong secondary antigen specific CD8+ T cell response was detected in both of the compartments tested after priming the mice with the recombinant PR8/NS-Nef (H1N1) vector followed by a boost using the H3N2 subtype Aichi/NS-Nef vector. In this case, Nef- and NP peptide-specific secondary responses were approximately 1.5 to 3 times higher than after a single immunization (FIGS. 11 and 12).

Single cell suspensions derived from the urogenital tracts were obtained from immunized mice. Two immunizations were necessary before significant numbers of Nef peptide-specific CD8+ T cells could be detected. The strongest Nef peptide specific CD8+ T cell response was detected when mice were primed i.n. with PR8/NS-Nef (H1N1) virus and subsequently boosted with the Aichi/NS-Nef (H3N2) virus (342±18 IFN-γ SC/10$^6$ cells; FIG. 13B). This immunization protocol was also found to induce the strongest NP peptide-specific CD8+ T cell response (FIG. 13A).

Figure 14:
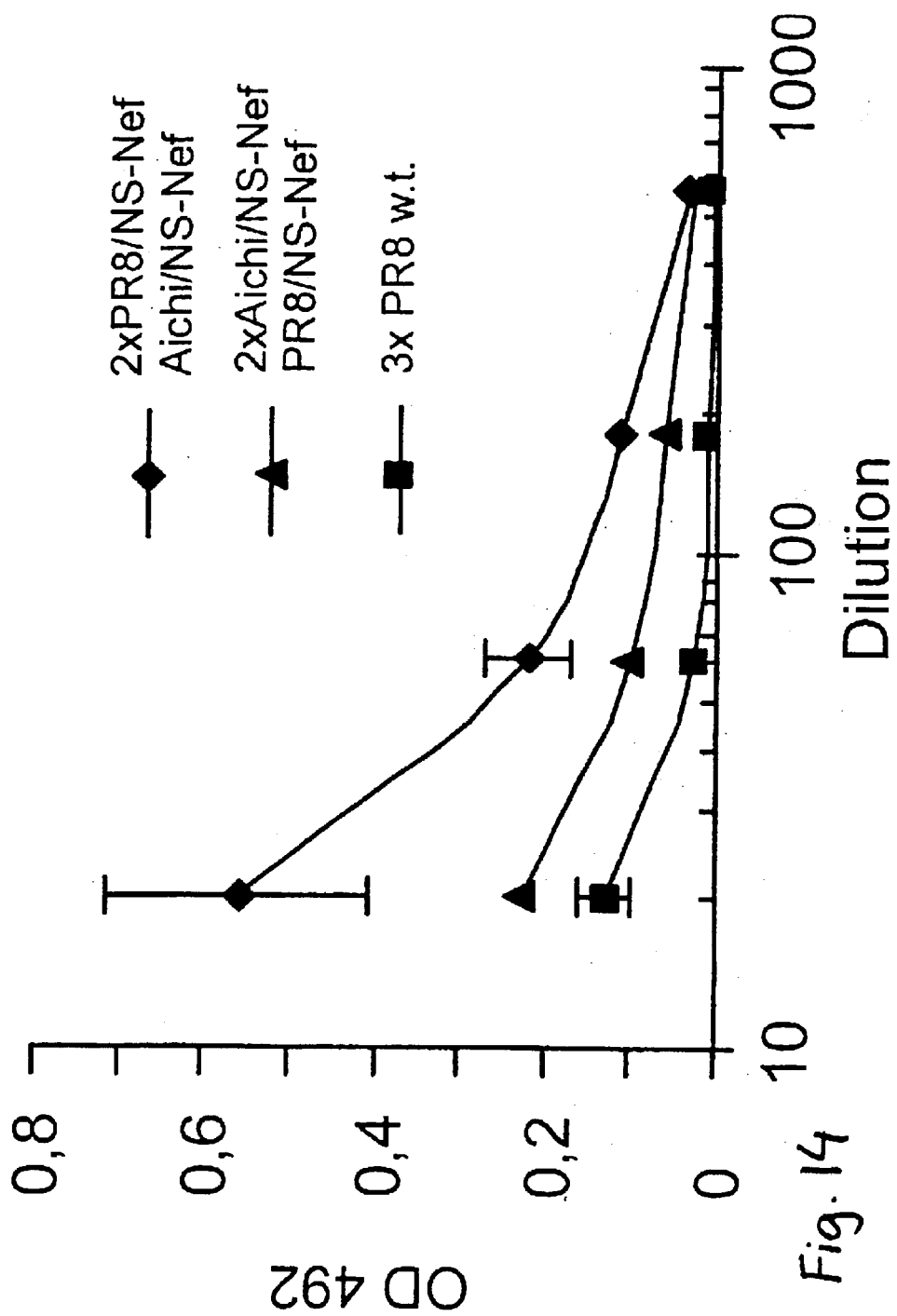
FIG. 14 exhibits results of an ELISA assay determining Nef-specific IgG in sera of mice two weeks after the third immunization with the PR8/NS-Nef or the Aichi/NS-Nef vector.

As described for the detection of T-cell responses mice were utilized to assess the Nef-specific serum antibody response. Mice were primed i.n. either with 10$^6$ PFU/ml of the PR8/NS-Nef (H1N1) or Aichi/NS-Nef (H3N2) virus and were boosted three weeks later with the same vector. The third immunization was performed following three more weeks utilizing the vector of the different subtype. The control group was immunized three times with the PR8 w.t. virus. The reactivities of serum samples (obtained two weeks after the third immunization) with the GST-Nef fusion peptide were determined by ELISA and are shown in FIG. 14. Nef-specific antibodies were detected only in groups of mice which had been successively immunized with H1N1 and H3N2 vectors (FIG. 14). The highest level of Nef-specific IgG was detected in mice immunized twice i.n. with 10$^6$ PFU of the PR8/NS-Nef (H1N1) virus and boosted with 106 PFU of the Aichi/NS-Nef (H3N2) virus as compared with the control group which had been immunized three times i.n. with PR8 w.t. virus (FIG. 14).

Both influenza virus vectors (PR8/NS-Nef and Aichi/NS-Nef) were completely attenuated in mice, since no viral titers could be detected in mouse respiratory tissues. These attenuated phenotypes of both recombinant viruses indicate that introduction of additional amino acids downstream of the position 125 of the NS1 protein can affect some function of the NS1 protein since PR8/NS-124 virus encoding the same size of the NS1 protein grew efficiently in mouse respiratory tracts (FIG. 4). The low efficiency of the 2A site to cleave Nef antigen from the N-terminal part of NS1 protein, especially at the late stage of infection, might be responsible for additional attenuation, although a direct effect of the Nef polypeptide interacting with some intracellular components can not be excluded.

The data indicate that completely attenuated recombinant influenza/NS-Nef viruses are capable to induce a primary CD8+ T cell response directed to the inserted Nef polypeptide in spleens and in lymph nodes draining the respiratory tracts of mice immunized i.n. without anesthesia. At the same time, vector (NP peptide)-specific CD8+ T cell responses in spleens and draining lymph nodes of mice immunized i.n. either with the PR8/NS-Nef or Aichi/NS-Nef vector were in the range of those induced by the virulent PR8 w.t. virus although the strongest NP-peptide specific CD8+ T cell response detected in the draining lymph nodes was found in mice immunized with the PR8/NS-124 virus efficiently replicating in the lungs.

The results indicate that it is possible to achieve a similar effect utilizing influenza vectors belonging to different antigenic subtypes. Importantly, influenza virus vectors are capable to induce a CD8+ T cell response circumventing the pre-existing immunity caused by a different influenza virus subtype.

The immunogenic potential of attenuated influenza/NS-Nef vectors might be explained by the fact that viruses containing truncated forms of the NS1 protein induce high levels of type 1 interferons in vivo. Nef-expressing vectors as well as PR8/NS-124 virus induced significantly higher levels of type 1 interferons in serum following immunization of mice if compared with the corresponding w.t. parent viruses (data not shown).

EXAMPLE 4

Plaque Reduction Assay

Figure 8:
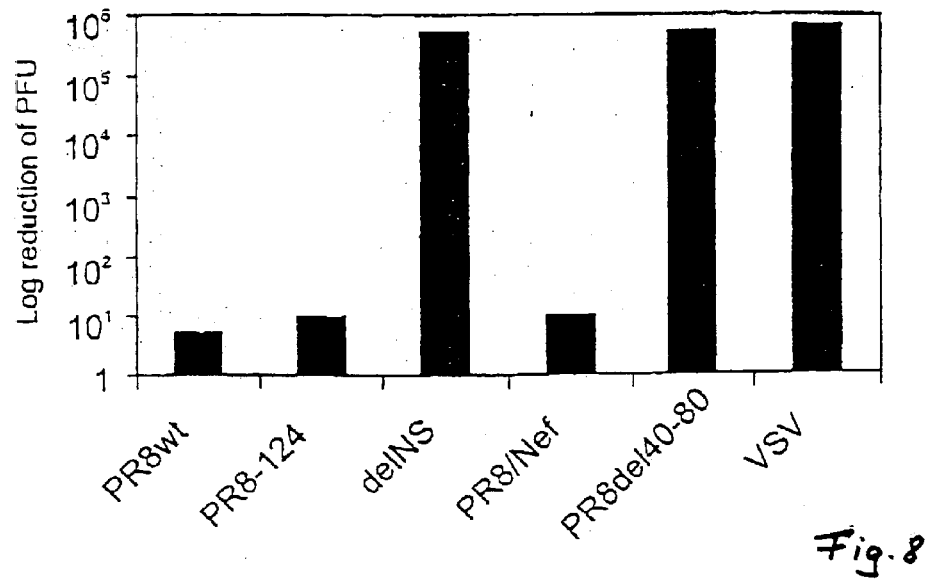
FIG. 8 exhibits results of a plaque reduction assay.

MDCK cells were treated for 24 h with a supernatant from MDCK cells infected by deINS virus (same construct as disclosed in WO 99/64571, i.e., containing entire NS1 deletion) as a known potent IFN alfa/beta inducer (FIG. 8). The content of the IFNalfa/beta was estimated to 100 U following an overnight treatment with pH 2. The results in FIG. 8 are given in log of plaque forming units (PFU) reflecting the differences in viral titers on IFNalfa/beta treated and untreated cells.

EXAMPLE 5

Interferon Induction

Figure 9:
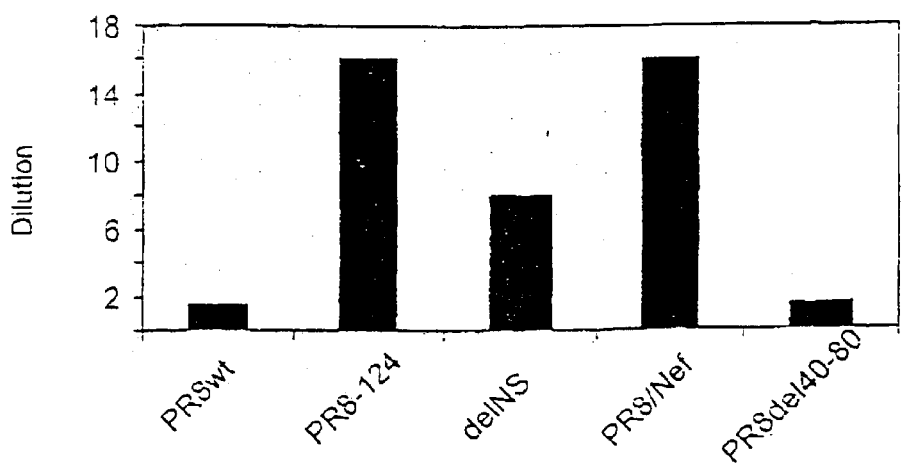
FIG. 9 exhibits results of an interferon induction assay.

MDCK cells were infected for 24 h with 5 MOI of different influenza viruses as outlined in FIG. 9. The supernatants were treated overnight with pH 2 at 4° C. for virus inactivation. Treated supernatants were adjusted to pH 7,4 with 1 N NaOH. Twofold serial dilutions of these supernatants were added to MDCK monolayers for 24 hrs and 50 PFU of the vesicular stomatitis virus (VSV) were then added per well. The results represent the dilution of the supernatant at which VSV plaque formation was reduced by 50%.

EXAMPLE 6

Figure 15:
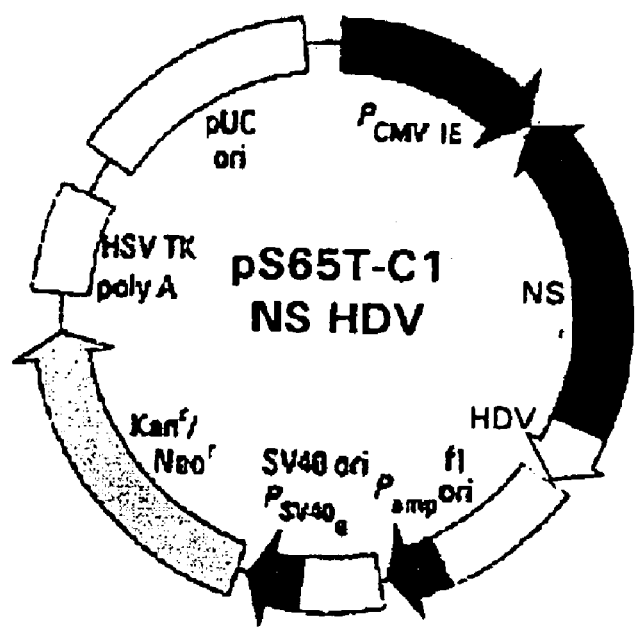
FIG. 15 is a schematic representation of an Influenza NS transcription system for expression of minus sense RNA for use in generating recombinant influenza viruses.

A Method for Accelerated Production of Recombinant Viruses and Anti-Viral Vaccines a) Generating Recombinant Cell Lines Producing Modified NS Gene:

A plasmid vector was constructed according to the schematic representation in FIG. 15. The NS gene was cloned into the backbone of a pS65T-C1 vector (Clontech), using the CMV promotor to initiate transcription. Inserting NS in reverse orientation (3' end towards CMV promotor) leads to the transcription of minus sense RNA. Transcription is terminated by a hepatitis delta virus (HDV) sequence that comprises a self-cleaving RNA site. Hence, this vector contains an influenza A NS gene where the cassette of the multiple stop codons is introduced at nt position 140 in a manner such that translation of this gene (reading frame 3) leads to a truncated form of the NS1 protein (comprising only 38 amino acids). It was found that influenza A viruses expressing such a short NS1 protein are highly attenuated in animals (Egorov et al. 1998, J Virol. 72, 8, p 6473).

```
Sequence of HDV (85 nt) (SEQ ID NO: 5):

TGGCCGGCATGGTCCCAGCCTCCTCGCTGGCGCCGGCTGGGCAACATTCC

GAGGGGACCGTCCCCTCGGTAATGGCGAATGGGAC

Sequence of PR8NS38 (906 nt) (SEQ ID NO: 6):

AGCAAAAGCAGGGTGACAAAGACATAATGGATCCAAACACTGTGTCAAGCT

TTCAGGTAGATTGCTTTCTTTGGCATGTCCGCAAACGAGTTGCAGACCAA

GAACTAGGTGATGCCCCATTCCTTGATCGGCTTCGCCGAGTGAATAACTA

GCTGAATCAGAAATCCCTAAGAGGAAGGGGCAGCACCCTCGGTCTGGACA

TCGAGACAGCCACACGTGCTGGAAAGCAGATAGTGGAGCGGATTCTGAAA

GAAGAATCCGATGAGGCACTTAAAATGACCATGGCCTCTGTACCTGCGTC

GCGTTACCTAACTGACATGACTCTTGAGGAAATGTCAAGGGACTGGTCCA

TGCTCATACCCAAGCAGAAAGTGGCAGGCCCTCTTTGTATCAGAATGGAC

CAGGCGATCATGGATTAAGAACATCATACTGAAAGCGAACTTCAGTGTGA

ATTTTGACCGGCTGGAGACTCTAATATTGCTAAGGGCTTTCACCGAAGAG

GGAGCAATTGTTGGCGAAATTTCACCATTGCCTTCTCTTCCAGGACATAC

TGCTGAGGATGTCAAAAATGCAGTTGGAGTCCTCATCGGGGACTTGAAT

GGAATGATAACACAGTTCGAGTCTCTGAAACTCTACAGAGATTCGCTTGG

AGAAGCAGTAATGAGAATGGGAGACCTCCACTCACTCCAAAACAGAAACG

AGAAATGGCGGGAACAATTAGGTCAGAAGTTTGAAGAAATAAGATGGTTG

ATTGAAGAAGTGAGACACAAACTGAAGATAACAGAGAATAGTTTTGAGCA

AATAACATTTATGCAAGCCTTACATCTATTGCTTGAAGTGGAGCAAGAGA

TAAGAACTTTCTCGTTTCAGCTTATTTAGTAATAAAAAACACCCTTGTTT

CTACT
```

This plasmid vector was used for transfection in order to transform Vero cells. Before transfection, cells were seeded in appropriate cell culture flasks (e.g. 25 cm) and incubated at 37° C. until having reached about 50% confluence. To improve the transfection efficiency the cationic lipid reagents (lipofectin, lipofectamine 2000) may be preincubated in medium without serum prior to mixing it with the plasmid-DNA. Accordingly, 2–6 µl cationic lipid reagent were diluted in 100 µl OPTI-MEM I serum free transfection medium and incubated 30 min at room temperature. Meanwhile 1–2 µg DNA were diluted in 100 µl OPTI-MEM I, then mixed with the lipid solution and incubated 15 min at room temperature. While DNA-lipid complexes formed, the cells were washed twice with serum-free transfection medium to remove residual proteins. The transfection cocktail was diluted to a total volume of 1 ml using transfection medium and added to the cells. Cells were incubated at 37° C. with 7% $CO_2$ from 5 to 8 h. Thereafter cell culture supernatant was removed and cells were fed with normal culture medium. 24 hours post transfection stable transfectants were selected by addition of selection medium containing geneticin sulfate G418 (400 µg/ml). Three weeks later stable transfectants appeared which were subcloned by limiting dilutions. Several subclones were tested for their ability to rescue the ts helper virus (25A-1 mutant, which is a reassortant virus wherein the NS gene responsible for the ts phenotype originates from cold-adapted influenza strain A/Leningrad/134/47/57, and the remaining genes originate from PR8 virus; Egorov et al., 1994, Vopr. Virusol.39: 201–205) at a temperature of 40° C. For that purpose, the cells were infected with the 25A-1 mutant and incubated at 40° C. for 72 hours. Those subclones yielding viral progeny that contained influenza viruses carrying the recombinant NS gene were selected and further multiplied under conditions allowing for efficient cell growth.

b) Recombinant Influenza Virus and Vaccine Production:

Transformed cells expressing a modified NS gene segment comprising a truncated NS1 gene with or without insertions, preferably as described hereinbefore, are infected with a desired influenza virus, particularly with a wildtype epidemic virus, under conditions as described above and incubated to allow for the development of viral progeny wherein the wildtype NS gene is replaced by the recombinant modified NS gene supplied by the transformed host cells. The viral yield can be cloned by plaquing methods (e.g. negative colonies under agar overlay) on a normal Vero cell line and each viral colony can be screened for the presence of the modified recombinant NS gene by the RT-PCR method and/or by other methods (depending on how the gene was modified). Positive viral plaques are then purified by further plaquing purification steps. Finally, the recombinant influenza strains are highly attenuated because of the truncated NS protein. They serve as vaccine candidates and are multiplied preferably using IFN deficient substrates such as Vero cells, young chicken embryos (less than 10 days old) and the like, for rapid manufacture of highly attenuated live influenza vaccines.

It is pointed out, however, that the method described in this Example is just one way to exemplify the underlying general concept of preparing and establishing mammalian cell lines, particularly immortalized or continuous cell lines, that after transformation with any desired viral gene sequences stably integrate and express these sequences, and thus allow for relatively simple and rapid design and manufacture of reasserted, recombinant viruses of whatever origin.

| ABBREVIATIONS | |
|---|---|
| aa | amino acid |
| CMV | cytomegalovirus |
| CTL | cytotoxic T-lymphocyte |
| gp | glycoprotein |
| HA | haemagglutinin |
| IFN | interferon |
| Ig | immunoglobulin |
| IL | interleukin |
| i.n. | intranasally |
| mAb | monoclonal antibody |
| MHC | major histocompatibility complex |
| NA | neuramidase |
| nef | negative factor of HIV |
| NP | nucleoprotein |
| NS | non-structural |
| ORF | open reading frame |
| RNP | ribonucleoprotein |
| SIV | Simian immunodeficiency virus |
| ts | temperature sensitive |
| v | viral |
| VSV | vesicular stomatitis virus |
| wt | wild type |

We claim:

1. A genetically engineered influenza virus comprising a modified NS gene, having a functional RNA binding domain and a gene sequence modification downstream of nucleotide position 400 of the NS1 gene, counted on the basis of influenza A/PR/8/34 virus, which modification bars translation of the remaining portion of the NS1 gene, wherein the influenza virus is attenuated and has an IFN inducing yet interferon insensitive phenotype of a nature such as is confirmed by its ability to induce an interferon response in MDCK cells and embryonated hen eggs and to grow on said MDCK cells and on said embryonated hen eggs, and wherein said modification comprises an insertion of a heterologous coding sequence operatively fused to the NS1 coding sequence.

2. A genetically engineered influenza virus according to claim 1, wherein the modification is between nucleotide positions 400 and 525 of the NS1 gene, counted on the basis of influenza A/PR/8/34 virus.

3. A genetically engineered influenza virus according to claim 1, wherein the insertion encodes a sequence of at least 80 amino acids.

4. A genetically engineered influenza virus according to claim 1, wherein the modification comprises an insertion of at least one sequence selected from the group consisting of an autocleavage site 2A (SEQ ID NO: 2), the nef gene from HIV-1 a sequences encoding the ELDKWA(SEQ ID NO: 1) or ELDKWAS (SEQ ID NO: 7) epitopes of gp41 of HIV-1, a sequence encoding IL-1β or a part thereof comprising SEQ ID NO: 8, a leader sequence, and an anchor sequence.

5. An immunogenic composition comprising at least one genetically engineered influenza virus defined in claim 1, in a suitable pharmaceutical formulation.

6. An immunogenic composition according to claim 5, comprising live attenuated recombinant influenza virus.

7. An immunogenic composition according to claim 6, wherein said virus is cold adapted.

8. An immunogenic composition according to claim 5, which induces an immune response against an antigen or pathogen encoded by a heterologous insertion of said genetically engineered influenza virus.

9. An immunogenic composition according to claim 8, wherein the heterologous insertion encodes a viral antigen.

10. An immunogenic composition according to claim 8, wherein said immune response is a cytotoxic T lymphocyte (CTL) response.

11. An immunogenic composition according to claim 8, wherein the viral infection is influenza or HIV-I infection.

12. A genetically engineered influenza virus according to claim 1 obtained in a method for the manufacture of recombinant viruses comprising the steps of: transforming a mammalian cell with a DNA vector comprising a viral gene segment, selecting transformed cells that express the viral gene segment, infecting the selected cells with a desired influenza virus, incubating the infected cells to allow for the development of viral progeny containing said viral gene segment, and selecting and harvesting viral progeny containing said viral gene segment, wherein transformation of the mammalian cell is accomplished comprising mixing said DNA vector with lipids to allow for a self-assembly of the lipid and the DNA to form lipid-DNA complexes, and incubating the mammalian cells in the presence of said lipid-DNA complexes resulting in an uptake of lipid-DNA complexes into the cells.

13. The genetically engineered influenza virus according to claim 12, wherein the DNA vector is a transcription system for minus sense influenza RNA.

14. A genetically engineered influenza virus according to claim 12, wherein said desired influenza virus is a wildtype epidemic strain.

15. A method for inducing an immune response against an infectious disease, comprising administering to a patient a genetically engineered influenza virus according to claim 1.

16. A method for inducing an immune response against an infectious disease, comprising administering to a patient an immunogenic composition according to claim 5.

17. A recombinant NS gene segment of an influenza A virus comprising a functional RNA binding domain and a gene sequence modification downstream of nucleotide position 400 of the NS1 gene, counted on the basis of influenza A/PR/8/34 virus, wherein the modification comprises an insertion of a heterologous coding sequence operatively fused to the NS1 coding sequence, wherein the insertion bars translation of the remaining portion of the NS1 gene and renders an influenza virus comprising said modified NS gene segment interferon inducing and interferon insensitive of such a nature as is confirmed by the ability of a said attenuated virus to induce an interferon response in MDCK cells and embryonated hen eggs and to grow on said MDCK cells and on said embryonated hen eggs.

18. The recombinant NS gene segment according to claim 17, wherein the insertion is between nucleotide positions 400 and 525 of the NS1 gene, counted on the basis of influenza A/PR/8/34 virus.

19. The recombinant NS gene segment according to claim 17, wherein the modification comprises an insertion encoding a sequence of at least 80 amino acids.

20. The recombinant NS gene segment according to claim 17, wherein the modification comprises an insertion of at least one sequence selected from the group consisting of an autocleavage site 2A (SEQ ID NO: 2), the nef gene from HIV-1, a sequences encoding the ELDKWA(SEQ ID NO: 1) or ELDKWAS (SEQ ID NO: 7) epitopes of gp41 of HIV-1, a sequence encoding IL-1β or a part thereof comprising SEQ ID NO: 8, a leader sequence, and an anchor sequence.

21. A method of making an attenuated recombinant influenza virus that has an interferon inducing yet interferon insensitive phenotype of a nature such as is confirmed by its ability to induce an interferon response in MDCK cells and in embryonated hen eggs and to grow on said MDCK cells and on said embryonated hen eggs, said method comprising:

providing a recombinant NS gene segment of an influenza A virus that comprises a functional RNA binding domain, and modifying its gene sequence after nucleotide position 400 of the NS1 gene segment, counted on the basis of influenza A/PR/8/34 virus, wherein the modification comprises an insertion of a heterologous coding sequence operatively fused to the NS1 coding sequence, wherein the insertion bars translation of the remaining portion of the NS1 gene segment.

22. The method according to claim 21, wherein the modification is between nucleotide positions 400 and 525, of the NS1 gene, counted on the basis of influenza A/PR/8/34 virus.

23. The method according to claim 21, wherein the insertion encodes a sequence of at least 80 amino acids.

24. The method according to claim 21, wherein the modification comprises an insertion of at least one sequence selected from the group consisting of an autocleavage site 2A (SEQ ID NO: 2), the nef gene from HIV-1, a sequences encoding the ELDKWA(SEQ ID NO: 1) or ELDKWAS (SEQ ID NO: 7) epitopes of gp41 of HIV-1, a sequence encoding IL-1β or a part thereof comprising (SEQ ID NO: 8), a leader sequence, and an anchor sequence.

25. The method according to claim 1, further comprising the steps of:

transforming a mammalian cell with a DNA vector comprising a viral gene segment, selecting transformed cells that express the viral gene segment, infecting the selected cells with a desired influenza virus, incubating the infected cells to allow for the development of viral progeny containing said viral gene segment, and selecting and harvesting viral progeny containing said viral gene segment, wherein transformation of the mammalian cell is accomplished comprising mixing said DNA vector with lipids to allow for a self-assembly of the lipid and the DNA to form lipid-DNA complexes, and incubating the mammalian cells in the presence of said lipid-DNA complexes resulting in an uptake of lipid-DNA complexes into the cells.

26. The method according to claim 25, wherein the DNA vector is a transcription system for minus sense influenza RNA.

27. The method according to claim 25, wherein said desired influenza virus is a wildtype epidemic strain.

* * * * *

SEQUENCE LISTING

<160> NUMBER OF SEQ ID NOS: 10

<210> SEQ ID NO 1
<211> LENGTH: 6
<212> TYPE: PRT
<213> ORGANISM: Human immunodeficiency virus type 1

<400> SEQUENCE: 1

Glu Leu Asp Lys Trp Ala
1               5

<210> SEQ ID NO 2
<211> LENGTH: 17
<212> TYPE: PRT
<213> ORGANISM: Foot-and-mouth disease virus

<400> SEQUENCE: 2

Asn Phe Asp Leu Leu Lys Leu Ala Gly Asp Val Glu Ser Asn Pro Gly
1               5                   10                  15

Pro

<210> SEQ ID NO 3
<211> LENGTH: 17
<212> TYPE: PRT
<213> ORGANISM: Human immunodeficiency virus type 1

<400> SEQUENCE: 3

Glu Trp Arg Phe Asp Ser Arg Leu Ala Phe His His Val Ala Arg Glu
1               5                   10                  15

Leu

<210> SEQ ID NO 4
<211> LENGTH: 14
<212> TYPE: PRT
<213> ORGANISM: Influenza A virus

<400> SEQUENCE: 4

Thr Tyr Gln Arg Thr Arg Ala Leu Val Arg Thr Met Gly Asp
1               5                   10

<210> SEQ ID NO 5
<211> LENGTH: 85
<212> TYPE: DNA
<213> ORGANISM: Hepatitis D virus

<400> SEQUENCE: 5
tggccggcat ggtcccagcc tcctcgctgg cgccggctgg gcaacattcc gaggggaccg      60
tcccctcggt aatggcgaat gggac                                           85

<210> SEQ ID NO 6
<211> LENGTH: 906
<212> TYPE: DNA
<213> ORGANISM: Influenza A virus /PR8NS38

<400> SEQUENCE: 6
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gtgaataact agctgaatca gaaatcccta agaggaaggg     180
gcagcaccct cggtctggac atcgagacag ccacacgtgc tggaaagcag atagtggagc     240

-continued

```
ggattctgaa agaagaatcc gatgaggcac ttaaaatgac catggcctct gtacctgcgt    300
cgcgttacct aactgacatg actcttgagg aaatgtcaag ggactggtcc atgctcatac    360
ccaagcagaa agtggcaggc cctctttgta tcagaatgga ccaggcgatc atggattaag    420
aacatcatac tgaaagcgaa cttcagtgtg aattttgacc ggctggagac tctaatattg    480
ctaagggctt tcaccgaaga gggagcaatt gttggcgaaa tttcaccatt gccttctctt    540
ccaggacata ctgctgagga tgtcaaaaat gcagttggag tcctcatcgg gggacttgaa    600
tggaatgata acacagttcg agtctctgaa actctacaga gattcgcttg agaagcagt     660 aatgagaatg ggagacctcc actcactcca aaacagaaac gagaaatggc gggaacaatt    720
aggtcagaag tttgaagaaa taagatggtt gattgaagaa gtgagacaca aactgaagat    780
aacagagaat agttttgagc aaataacatt tatgcaagcc ttacatctat tgcttgaagt    840
ggagcaagag ataagaactt tctcgtttca gcttatttag taataaaaaa caccccttgtt   900 tctact                                                              906
```

<210> SEQ ID NO 7
<211> LENGTH: 7
<212> TYPE: PRT
<213> ORGANISM: Human immunodeficiency virus type 1

<400> SEQUENCE: 7

Glu Leu Asp Lys Trp Ala Ser
1               5

<210> SEQ ID NO 8
<211> LENGTH: 9
<212> TYPE: PRT
<213> ORGANISM: Artificial
<220> FEATURE:
<223> OTHER INFORMATION: IL-1beta derived peptide

<400> SEQUENCE: 8

Val Gln Gly Glu Glu Ser Asn Asp Lys
1               5

<210> SEQ ID NO 9
<211> LENGTH: 21
<212> TYPE: PRT
<213> ORGANISM: Artificial
<220> FEATURE:
<223> OTHER INFORMATION: Leader sequence

<400> SEQUENCE: 9

Pro Met Lys Thr Ile Ile Ala Leu Ser Tyr Ile Phe Cys Leu Ala Leu
1               5                   10                  15

Gly Gln Asp Leu Pro
            20

<210> SEQ ID NO 10
<211> LENGTH: 38
<212> TYPE: PRT
<213> ORGANISM: Artificial
<220> FEATURE:
<223> OTHER INFORMATION: Anchor sequence

<400> SEQUENCE: 10

Gln Ile Leu Ala Ile Tyr Ser Thr Val Ala Ser Ser Leu Val Leu Leu
1               5                   10                  15

```
                            -continued
Val Ser Leu Gly Ala Ile Ser Phe Trp Met Cys Ser Asn Gly Ser Leu
                20                  25              30

Gln Cys Arg Ile Cys Ile
        35
```